United States Patent [19]

Sarnoff

[11] Patent Number: 4,658,830
[45] Date of Patent: Apr. 21, 1987

[54] METHOD AND APPARATUS FOR INITIATING REPERFUSION TREATMENT BY AN UNATTENDED INDIVIDUAL UNDERGOING HEART ATTACK SYMPTOMS

[75] Inventor: Stanley J. Sarnoff, Bethesda, Md.

[73] Assignee: Survival Technology, Inc., Bethesda, Md.

[21] Appl. No.: 638,695

[22] Filed: Aug. 8, 1984

[51] Int. Cl.⁴ .............................................. A61B 5/04
[52] U.S. Cl. .................................... 128/696; 604/137
[58] Field of Search ............... 604/136, 137, 138, 139; 128/696, 904

[56] References Cited

U.S. PATENT DOCUMENTS

| | | | |
|---|---|---|---|
| 3,391,695 | 6/1968 | Sarnoff | 604/200 |
| 3,792,700 | 2/1974 | Sarnoff et al. | 128/639 |
| 3,882,863 | 5/1975 | Sarnoff et al. | 604/136 |
| 3,910,260 | 10/1975 | Sarnoff et al. | 128/904 |
| 3,938,507 | 2/1976 | Sarnoff et al. | 128/701 |
| 4,004,577 | 1/1977 | Sarnoff | 128/904 |
| 4,226,235 | 10/1980 | Sarnoff et al. | 604/136 |
| 4,329,988 | 5/1982 | Sarnoff et al. | 604/137 |
| 4,394,863 | 7/1983 | Bartner | 604/90 |

OTHER PUBLICATIONS

Keith A. A. Fox et al., Biochemical Pharmocology, Commentary, "Coronary Thrombolysis: Pharmacological Considerations with Emphasis on Tissue-Type Plasminogen Activator (8-PA)", vol. 33, No. 12, pp. 1831–1838.

Frans Van de Werf, M.D. et al., The New England Journal of Medicine, "Coronary Thrombolysis with Tissue-Type Plasminogen Activator in Patients with Evolving Myocardial Infarction", Mar. 8, 1984, vol. 310, No. 10, pp. 609–613.

Lawrence K. Altman, The New York Times, "Protein of Cancer Cells Used to Halt Coronaries", Nov. 16, 1983.

Primary Examiner—William E. Kamm
Attorney, Agent, or Firm—Cushman, Darby & Cushman

[57] ABSTRACT

A device for initiating reperfusion treatment of a coronary prone individual prior to the establishment of qualified direct contact personal care at a time during the early minutes or hours after the onset of heart attack symptoms and after qualified personnel have participated by telephone in the decision to initiate such treatment. The device comprises an automatic injector assembly including a releasable force applying assembly, a safety normally disposed in a release preventing position movable therefrom into a release permitting position, a container or containers for separately containing a plurality of separate medicament dosages including a first dosage containing a clot selective coronary thrombolytic agent and a separate second dosage containing a cardiac antiarrhythmic agent and one or more hypodermic needles. The automatic injector is operable in response to a predetermined manual actuating procedure including the movement of the safety into its release permitting position for effecting release of the releasable force applying assembly and causing the released force to be applied so as to effect the movement of the hypodermic needle or needles into the muscle tissue of the individual and the flow of the separate medicament dosages outwardly from the container or containers through the hypodermic needle or needles into the muscle tissue of the individual.

18 Claims, 4 Drawing Figures

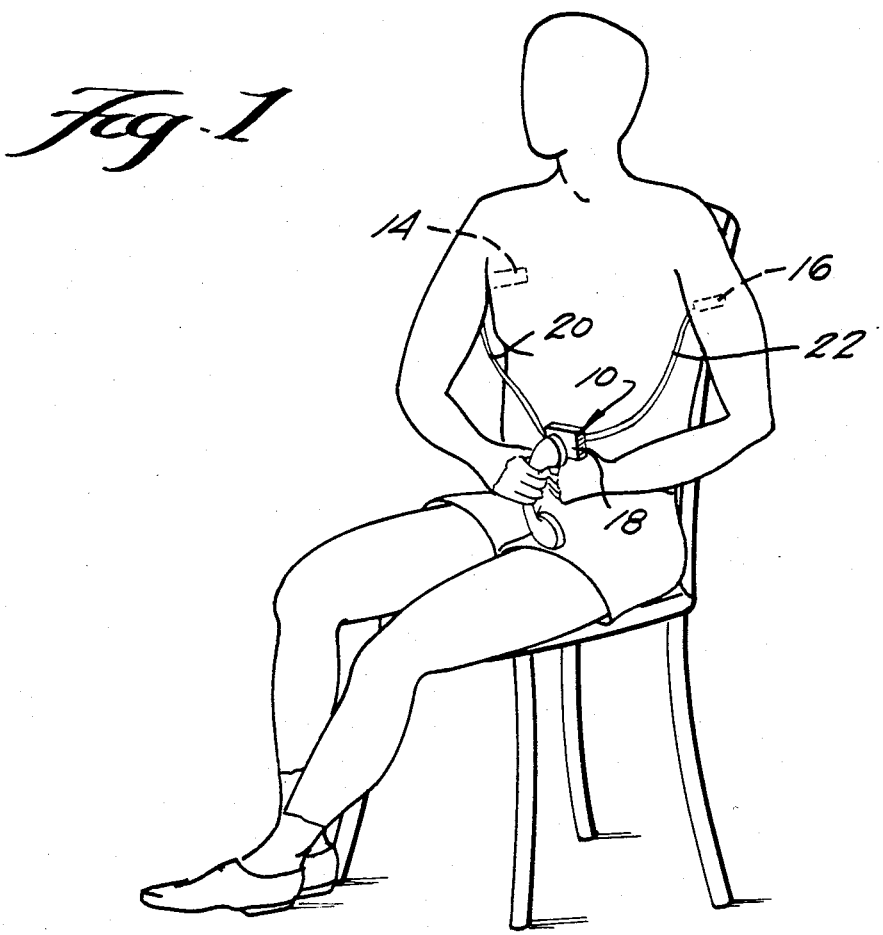
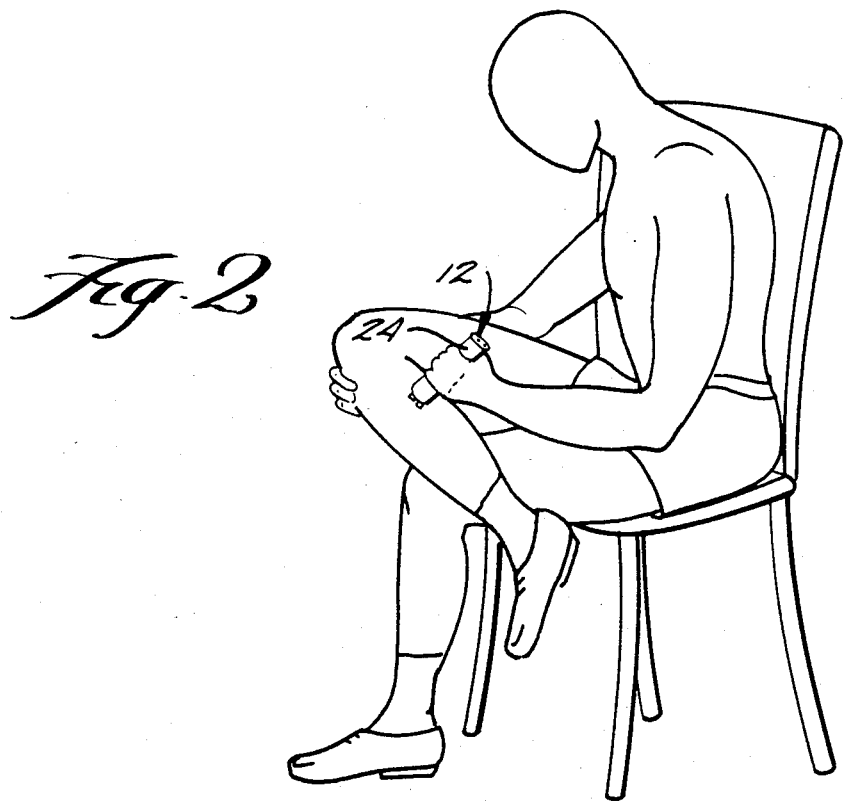

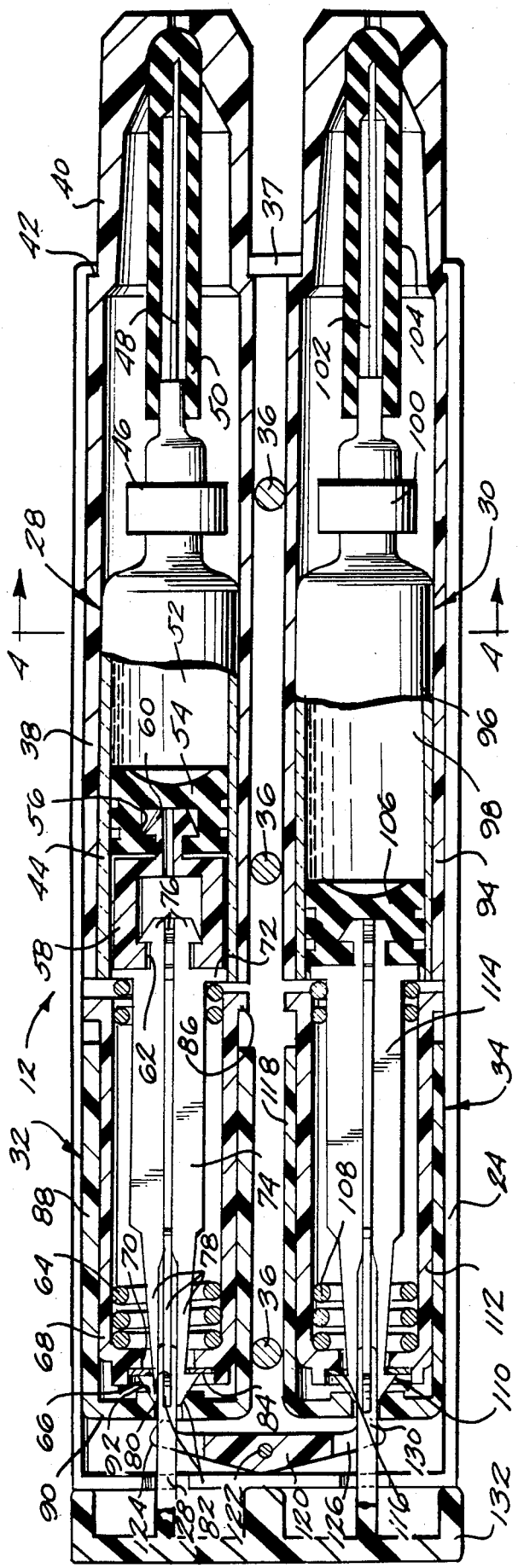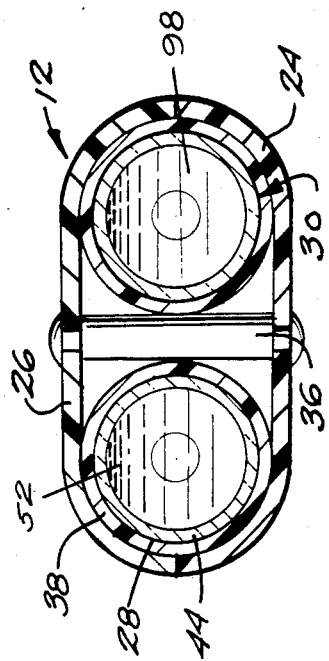

METHOD AND APPARATUS FOR INITIATING REPERFUSION TREATMENT BY AN UNATTENDED INDIVIDUAL UNDERGOING HEART ATTACK SYMPTOMS

This invention relates to the treatment of coronary prone individuals in the throes of a myocardial infarction in such a way as to minimize damage to the heart muscle and, more particularly, to improvements in such treatments enabling the same to be commenced at the earliest possible time, even before direct qualified personal care of the individual can be established.

When a clot forms in a blood vessel, the body organ being supplied with blood by that blood vessel is compromised or totally deprived of blood supply. Depending on the blood vessel in which this occurs, the threat to the life of the individual is either small or very great as in the circumstances to be addressed by the material below, i.e. certain life threatening circumstances. Clot formation in a vessel is described as thrombosis. Substances which dissolve thrombi are called thrombolytic substances. When a coronary artery clot is dissolved, the resultant establishment of blood flow to the heart is called reperfusion.

Examples of life threatening clot formation in arterial vessels are cerebral thrombosis, renal thrombosis, opthalmic artery thrombosis, and very importantly, thrombosis of a coronary artery. In approximately 85% to 90% of cases of acute myocardial infarction (coronary heart attack), a thrombus is found in the coronary artery preventing blood from flowing to the heart muscle (myocardium) and supplying it with essential oxygen and other nutrients. A consequence of a thrombus or clot forming in a coronary artery is the danger to the myocardium (heart muscle tissue that does the pumping of blood). Heart muscle deprived of its blood supply does not die immediately but does begin the process of becoming dead. The extent of the damage which is done to the heart muscle is, therefore, a function of the time during which the supply of blood to the infarct zone is restricted by the clot or occlusion.

Heretofore, the procedures undertaken to actually establish reperfusion to the infarct zone have always been undertaken in a hospital environment or equivalent. The so-called "pre-hospital" treatment was, in general, directed toward keeping the patient alive and getting the patient into the hospital environment as soon as possible so that treatment minimizing the heart muscle damage could be accomplished.

The treatment undertaken in the hospital environment involves certain procedures for establishing reperfusion in the infarct zone of the patient's heart. Where immediate surgery was not clearly indicated, the establishment of reperfusion was accomplished by procedures which had the effect of unblocking the occlusion. The available procedures included mechanical catheterization and the administration of thrombolytic agents. Known thrombolytic agents, such as streptokinase or urokinase required intercoronary infusion or the slow infeed of the agent within the vessel at the site of occlusion by means of a catheter. In recent years, intravenous infusion of streptokinase has been shown to be effective.

More recently a substance called tissue-type plasminogen activator or t-PA has been utilized experimentally. (*The New England Journal of Medicine*, March 8, 1984, Vol. 310, No. 10, pp. 609613). Unlike other plasminogen activators, such as streptokinase or urokinase, t-PA—which is found in only small amounts in the body—acts specifically on clots and not on other proteins in the blood, when maintained at appropriate and effective levels.

A 1984 Commentary found in *Biochemical Pharmacology* Vol. 33, No. 12, pp. 1831-1838 entitled "Coronary Thrombolysis: Pharmacological Considerations with Emphasis on Tissue-Type Plasminogen Activator (t-PA)" contains the following conclusionary statement:

"Selection of pharmacological agents for induction of coronary thrombolysis has been determined largely by availability. Unfortunately, both streptokinase and urokinase induce a systemic lytic state with depletion of circulating fibrinogen, plasminogen, and $\alpha_2$-antiplasmin, and accumulation of fibrin degradation products. All of these factors conspire to set the stage for hemorrhage with a risk of serious bleeding. Intravenous administration of these agents is limited by a lower success rate, in part because the upper bound of dose is constrained by the risk of inducing a severe systemic lytic state.

The probability that progress in recombinant DNA technology will lead to widespread availability of tissue-type plasminogen activator is particularly exciting because of the clot specific properties of t-PA. For coronary thrombolysis its potential advantages include: safety and efficacy of intravenous administration of high doses; effective clot lysis without induction of a systemic lytic state; prompt implementation without the need for extensive characterization of the coagulation and fibrinolytic systems in each patient prior to and during therapy; avoidance of frank allergic reactions or variations in dose-response relation due to immune complex formation; ease of minute-by-minute adjustment of dosage and prompt termination of fibrinolysis when needed because of the short biological half-life of t-PA and the lack of induction of a systemic lytic state."

The promise attributable to t-PA administration was discussed at a news conference at a meeting of the American Heart Association and reported by the New York *Times* on Nov. 16, 1983, in an article entitled, "Protein of Cancer Cells Used to Halt Coronaries." The article refers to injection of t-PA by stating the following: "The protein [t-PA] can simply be injected into the vein in the arm of the patient seized by a myocardial infarction or heart attack, and it travels through the blood to dissolve a clot, in much the same way as Draino clears up stopped plumbing."

The article further indicated under the subheading "Hopes for Future Application" that many physicians have expressed excitement about research into the use of t-PA to treat heart attacks because they hope that some day it may be used in emergency rooms and ambulances to stop heart attacks at their earliest stages before they kill or cause permanent damage. Under the "Hopes for Future Application" subheading there is also included the following paragraph: "Dr. Burton E. Sobel of Washington University, one of the researchers, speculated that patients might some day carry a vial with them so that the drug could be injected immediately after they felt chest pain and other early symptoms of a heart attack."

In medical parlance, a vial is a container for a quantity of liquid medicine or diluent having a rubber stopper capable of being pierced by a hypodermic needle of a syringe to enable the operator of the syringe to withdraw a predetermined dosage of the liquid from the vial. In the case of t-PA, the dosage could then be injected into the mother liquid container of an infusion assembly. The necessity to administer the drug by slow intravenous infusion or by slow intravenous injection presents a significant barrier to self-administration from a practical view point, particularly when considering the disconcerting circumstances of the individual undergoing the symptoms of a myocardial infarction.

The development of an effective self-administration procedure for t-PA sufficient to enable its utilization by a targeted coronary prone individual immediately following onset of symptoms, would materially increase the potential efficacy of t-PA as a thrombolytic agent by insuring its use at the earliest possible time often before irreversible heart muscle damage has occurred, and, at the same time, provide a treatment of the pre-hospital or pre-ambulance type which for the first time is directly effective to minimize heart muscle damage accompanying myocardial infarction. It is an object of the present invention to provide such a self administering treatment.

In accordance with the principles of the present invention, this objective is accomplished by providing the targeted coronary prone individual with apparatus for enabling an individual to initiate reperfusion treatment prior to the establishment of direct contact with qualified personnel care during the time during the early minutes or hours after the onset of heart symptoms and for enabling qualified personnel to participate by telephone in the decision to initiate such treatment. The treatment initiating function is preferably performed by an automatic injector assembly, including known components and at least two medicament containers, the assembly further including at least two medicament dosages in the containers including a first dosage containing a clot selective thrombylic agent, such as t-PA, mixed with an absorption enhancing agent, such as hydroxylamine hydrochloride and a second dosage containing a cardiac antiarrhythmic agent such as lidocaine. The decision enabling function is preferably performed by of an EKG monitor, preferably of a known type having electrodes capable of simple electrical connection with the coronary prone individual and housed circuitry capable of generating signals corresponding to the electrical activity triggering the coronary prone individual's heart beats sensed by the electrodes, which signals are capable of transmission over the telephone.

In accordance with the principles of the present invention, a coronary prone individual is requested to carry the aforesaid apparatus at all times so that soon after the onset of symptoms the individual undergoing such symptoms can carry out the following method, in accordance with the principles of the present invention to initiate the reperfusion treatment. As soon as possible, the coronary prone individual should connect the electrodes of the monitor in a position suitable to sense the electrical activity triggering the individual's heart beat so that the circuitry will produce signals corresponding to the electrical activity within the individual. Next, (or prior thereto) a telephone communication is established with qualified personnel at a central station through a telephone number indicated on the apparatus. In accordance with known procedures, the qualified personnel are stationed at the receiving end of the telephone. In accordance with these known procedures, qualified personnel at the receiving end have the capability of recording the signals produced by the monitor and transmitted over the telephone line by the individual undergoing coronary symptoms. At the same time, the qualified personnel are enabled to secure the medical record including the standing orders of the individual's doctor in the event of predetermined symptoms and EKG readings transmitted by the individual. Thus, within a short period of signal transmission, the qualified personnel on the receiving end are enabled to transmit orally a decision to the individual undergoing symptoms that it is appropriate to initiate reperfusion treatment. As soon as the individual has received this decision over the telephone, the individual then removes the safety from the automatic injector assembly and undergoes the remainder of the predetermined manual actuating procedure necessary to effect the injection of the two medicament dosages into the individual's muscle tissue.

It is an important advantage of the present invention that devices and methods utilized in accordance with the principles of the present invention are known per se. Reduced to its simplest terms, the invention involves packaging a clot selective thrombolytic agent such as t-PA and a cardiac antiarrhythmic agent such as lidocaine in a known emergency type automatic injector and injecting the two medicament agents into the muscle tissue after having received a decision to do so over the telephone from a qualified source and at a time prior to the establishment of direct contact qualified personal care. While the simplicity of the method and apparatus and its reliance upon components and procedural steps which have been proven effective per se constitutes the essence of the invention, this simplicity and use of proven individual components and procedural steps should not be equated to obviousness because of the following.

First of all, even though t-PA may be regarded as a clot selective thrombolytic agent, when introduced into the blood stream at a predetermined level, tests thus far performed show that the concentration can be increased to the point that a systemic lytic state can be induced. Intramuscular injection involves the introduction of a concentrated dosage of t-PA in an area contiguous to and substantially surrounding the wound caused by the penetration and withdrawal of the injection of the hypodermic needle. Consequently, it would be expected that at least a localized lytic state would be induced resulting in hemorrhage from the needle wound. Unexpectedly, tests have shown that no such hemorrhage does in fact occur.

Second, t-PA is a large protein. It would not be expected that it would be absorbed into the blood stream in discernible quantities. Extravascular levels of protein are about 1/10 that of intra-vascular protein. It is thought that this is so because the capillary pores through which transport of protein can occur are small relative to the molecular size of protein and limit protein transport because of electrical charge. It was thus highly problematical as to whether a large protein such as t-PA, when given intra-muscularly, i e. outside the blood vessels, would find its way rapidly into the blood stream in discernible quantities. Applicant tests have shown that unexpectedly t-PA does find its way rapidly into the blood stream in discernible quantities after intramuscular injection.

Finally, having ascertained that unexpectedly intramuscular injection could be utilized to increase the blood level of clot selective thrombolytic agents such as t-PA, a complete treatment system applicable to unattended coronary prone individuals could now be formulated. In accordance with the principles of the present invention, such a system includes the utilization of a heart monitor capable of transtelephonic transmission to a predetermined station having information and qualified personnel sufficient to make a decision based upon the signals transmitted and the oral communications transmitted in regard to the individual's symptoms as to the initiation of the treatment by the individual. The actual treatment of the system also includes intramuscular injection of a cardiac antiarrhythmic agent simultaneously or substantially simultaneously with the intramuscular injection of the thrombolytic agent. The provision of a simultaneous or substantially simultaneous injection of a cardiac antiarrhythmic agent is of significant importance because in conjunction with the unblocking of a coronary artery clot and the establishment of reperfusion, reperfusion of fibrillation, a condition quite clearly to be avoided in the unattended individual undergoing myocardial infarction. Accordingly, in order to render the administration of t-PA effective to such an unattended individual, the simultaneous or near simultaneous administration of a cardiac antiarrhythmic agent forms an important part of the present invention.

It is well known that the longer a myocardial infarction causing clot is allowed to remain blocked, the more difficult and time consuming it is to unblock it. The experience thus far with respect to i-c or i-v infused t-PA confirms the collarary that the level of t-PA and the time required to unblock a newly formed clot both are less and both increase as the time of blockage increases. Stated differently, the longer the initiation of the administration of the clot selective thrombolytic agent takes place after the formation of the clot, the longer the thrombolytic agent takes to unblock the clot and establish reperfusion. The time of initiation of the treatment, therefore, is doubly important.

In many hospitals treatment situations significant irreversible heart damage can occur during the longer time period required to unblock the clot and to establish reperfusion. Thus, as the time of initiation of the treatment is advanced in relation to the clot formation, there is an additional time saving in the subsequent accomplishment of reperfusion which ultimately prevents irreversible heart muscle damage. The present invention provides an effective means and method of accomplishing an initiation of the treatment at the earliest possible time because, for the first time, it does away with the time factor heretofore required to transport qualified personnel into direct contact with the individual exhibiting the symptoms of myocardial infarction or vice-versa. The treatment is thus achieved in the earliest possible time.

The above and other objects of the present invention will become more apparent during the course of the following detailed description and appended claims.

The invention may best be understood with reference to the accompanying drawings wherein an illustrative embodiment is shown.

In the drawings:

FIG. 1 is a perspective view illustrating the initial steps undertaken by an individual within the early minutes or hours after the onset of heart attack symptoms in carrying out the method of the present invention with the use of the heart monitor forming a component of the apparatus embodying the principles of the present invention;

FIG. 2 is a view similar to FIG. 1 showing the final steps undertaken by the individual in carrying out the method of the present invention with the use of the dual dosage automatic injector assembly forming a component of the apparatus embodying the principles of the present invention;

FIG. 3 is an enlarged longitudinal cross-sectional view of the injector assembly shown in FIG. 2; and FIG. 4 is a cross-sectional view taken along the line 4—4 of FIG. 3.

Referrring now more particularly to the drawings there is shown in FIGS. 1 and 2 thereof apparatus embodying the principles of the present invention for carrying out the steps of the method of the present invention depicted therein. The apparatus includes a heart monitoring assembly, generally indicated at 10, shown being used in FIG. 1, and a dual dosage automatic injector assembly, generally indicated at 12, shown being used in FIG. 2.

In accordance with the principles of the present invention the apparatus comprising the heart monitor assembly 10 and the automatic injector assembly 12 are provided to a multiplicity of individuals targeted as coronary prone with instructions that each individual is to either carry the apparatus on the individuals person at all times or to have it otherwise readily available without any significant time delay. The apparatus has marked thereon or otherwise included therewith a telephone number which can be dialed to establish a telephone communication line with a central station. The apparatus and personnel maintained at the central station and the method performed thereby is in accordance with the dislosure contained in commonly assigned U.S. Pat. No. 4,004,577 (see also 3,910,260).

The present invention is concerned with the apparatus utilized and procedures carried out by the targeted individuals on the other end of the phone from the central station. Consequently, for present purposes a detailed understanding with respect to the apparatus and procedures at the central station is not believed necessary. For such details reference may be had to the above noted patents. For present purposes it is sufficient to note that the central station is continuously manned with personnel qualified to receive a transmitted EKG monitor signal over the telephone and form a electrocardiogram therefrom which can be studied along with the stored information about the individual calling. Such information includes standing orders of the individual's personal physician as to the initiation of reperfusion treatment under contemplated emergency circumstances confirmed, by current heart attack symptoms orally communicated over the phone and analysis of the current EKG transmitted. Based upon all of the information thus available at the central station, the personnel there are also qualified to arrive at a decision on the case of each individual to initiate the reperfusion treatment, which decision is communicated to the individual over the telephone communication line established.

The heart monitor assembly 10 may assume any well known configuration. Since the monitor assembly constitutes a known device which is not modified when constituting a component of the apparatus of the present invention, a precise detailed disclosure is not believed necessary. For such details reference may be had to commonly assigned U.S. Pat. No. 3,938,507 which discloses a preferred monitor assembly in detail. For present purposes it is sufficient to note that the monitor assembly includes a pair of separate electrodes 14 and 16 capable of being connected to the individual at positions sufficient to sense the electrical activity triggering the heart beats of the individual. While the electrodes 14 and 16 may be connected with the individual in any known manner in any known positions, the preferred electrodes shown are constructed in accordance with the teachings of commonly assigned U.S. Pat. No. 3,792,700 so as to be capable of connection by simple self-retention within the individual's armpits. The monitor assembly 10 also includes a housed circuitry component 18 which is electrically connected to the electrodes 14 and 16 by electrical leads 20 and 22 respectively. While the circuitry may perform a number of desired functions for present purposes it is sufficient to note that it is capable of generating signals corresponding to the electrical activity sensed by the electrodes 14 and 16 capable of being transmitted over an established telephone communication line. The signals transmitted are of a quality sufficient to be received over the telephone communication line and rapidly converted into a printed electrocardiogram.

FIGS. 3 and 4 illustrate the details of a preferred dual dosage automatic injector assembly 12 which is constructed generally in accordance with the teachings of commonly assigned U.S. Pat. No. 4,226,235. As shown, the injection assembly 12 includes an outer housing in the form of two separate outer housing halves 24 and 26 molded of a suitable moldable material, such as plastic. The housing halves, when disposed together, provide chambers suitable to receive therein first and second cartridge units or sub-assemblies 28 and 30 and respective first and second power pack units or sub-assemblies 32 and 34. The two housing halves 24 and 26 are arranged to be rigidly secured together in operative relation with respect to the sub-assemblies by a plurality of spacer rivets 36 which serve not only to rigidly secure the two housing halves together in operative relation but to retain the first and second sub-assemblies within the outer housing in operative spaced relation. As shown, the housing halves 24 and 26 are provided with mating flanges 37 at their forward ends.

Mounted within a first one of the chambers provided by the housing halves 24 and 26 is a first container support 38 in the form of a tubular member having the major portion thereof formed with a cylindrical exterior periphery slidably fitting within the forward end portion of the chamber provided by the housing halves 24 and 26. The tubular member 38 includes a forwardly outwardly extending nose portion 40 of an exterior cylindrical configuration sufficient to extend through an opening in the flanges 37. The exterior transition between the nose portion 40 and the remainder of the tubular member 38 provided an annular shoulder 42 which is adapted to normally engage the associated adjacent portions of the flanges 37.

Slidably mounted within the tubular member 38 is a first glass or plastic ampule or dosage container 44. Preferably, the container is formed of glass, generally in the form of a necked bottomless bottle. Fixed to the necked end of the container 44 is a hub assembly 46 carrying a longitudinally forwardly extending hypodermic needle 48. The exterior of the hypodermic needle 48 is covered by a shock absorbing resilient sheath 50 in accordance with the teachings contained in commonly assigned Sarnoff et al. Pat. No. 3,882,863. The hub assembly 46 provides an interior resilient diaphragm (not shown) constructed in accordance with the teachings contained in commonly assigned Sarnoff et al. Pat. No. 3,391,695. The diaphraghm serves to seal the metallic material which forms the hypodermic needle 48 from the interior of the container 44 which has therein a dosage, indicated by the numeral 52, containing a clot selective coronary thrombolytic agent, such as for example t-PA mixed with an absorption enhancing agent, such as hydroxylamine hydrochloride.

The dosage 52 is sealingly retained in the container by a movable plunger member 54 which, as shown, is in the form of a piston of resilient material formed to provide an interior rearwardly facing socket 56. The preferred exemplary dosage 52 contains an amount of t-PA sufficient to be absorbed into the blood from an appropriate ultramuscular injection site to establish a t-PA blood plasma level of from 5 to 750 International (urokinase equivalent) units per milliliter of blood plasma. Based upon the animal studies thus far undertaken, it would appear that an intramuscular dosage of 1 milligram of t-PA per kilogram of body weight is one example of a dosage which would be suitable to produce a t-PA plasma level of from 5 to 750 International (urokinase equivalent) units per milliliter of blood plasma.

As shown, the dosage 52 is of a volume somewhat less than the total capacity of the container 44 and consequently plunger 54 is shown disposed in forwardly spaced relation within the rearward end of the container 44. A spacer member 58 is mounted in the end of the container and has a pronged forward portion 60 engaged within the socket 56 and a socket portion 62 formed in the rear portion thereof. The spacer member 58 thus forms a part of the plunger means which serves to move the liquid dosage 52 outwardly through the hypodermic needle 48 after the diaphragm has been ruptured through hydraulic pressure. It will be understood that the quantity of the dosage 52 can be varied by varying the lonqitudinal size of the spacer member 58 or by eliminating the spacer member entirely when a maximum volume dosage is desired.

The power pack sub-assembly 32 includes a first coil spring 64 retained in stressed condition by a first releasing mechanism, generally indicated at 66. The releasing meachanism 66 includes an inner tube or sleeve 68 having an interior cylindrical periphery of a size sufficient to receive the spring 64 therein. At the rearward end of the sleeve 68 is a radially inwardly extending flange 70 which serves to abuttingly receive the rearward end of the stressed spring 64. The forward end of the stressed spring 64 extends outwardly from the opposite end of the inner tube or sleeve 68 and is engaged by a plurality of outwardly extending tabs 72 formed on the forward end portion of an elongated collet member 74 made up of two interfitted stampings. The forward end of the collet member 74 adjacent the tabs 72 is formed with tongues 76 of a size to engage within the socket 62 in the end of spacer 58. The collet member 74 extends rearwardly from the tabs 72 through the interior of the spring 64 and has formed on the opposite rearward end thereof spring fingers 78 having forwardly facing locking shoulders 80 formed on the exterior thereof and rearwardly and inwardly inclined cam releasing surfaces 82 on the exterior rearward extremities thereof. The locking shoulders 80 are adapted to engage a suitable locking disk 84 engaged with the rearward surface of the flange 70 of the inner tube 68.

The forward end of the inner tube 68 is formed with a radially outwardly extending annular flange 86 which is spaced from the forward end of an outer tube 88 forming a part of the releasing mechanism 66. The outer tube 88 is slidably mounted over the exterior periphery of the inner tube 68 and has at its rearward end a centrally apertured end wall 90 having a forwardly and outwardly inclined frustoconical cam surface 92 formed on the central portion thereof disposed in engagement with the inclined cam surfaces 82 on the spring fingers 78. The container support member 38, container 44, dosage 52, hub 46, needle 48, sheath 50, plunger 54 and spacer 58 constitute the first dosage cartridge sub-assembly 28 and the spring 64, inner tube 68, collet member 74, outer tube 88 and locking disk 84 constitute the first power pack sub-assembly 32 for operating the first cartridge sub-assembly 28.

The second cartridge sub-assembly 30 is similar to the first and includes a second container support member 94, a second container 96, a second dosage 98, a second hub 100, a second needle 102, a second sheath 104, and a second plunger 106. The second power pack sub-asembly 34 is similar to the first and includes a second spring 108, a second releasing mechanism 110, a second inner tube 112, a second collet member 114, a second locking disk 116 and a second outer tube 118.

In accordance with the principles of the present invention, the second dosage 98 contains a cardiac antiarrhythmic agent, as, for example, lidocaine. An exemplary intramuscular dosage of lidocaine for present coronary antiarrhythmic purposes is 300 milligrams contained in 3 milliliters of liquid.

It will be noted that the housing halves 24 and 26 are extended rearwardly to receive therein a lever 120. Lever 120 has its central portion pivoted to the extended rearward end of the housing halves 24 and 26 by a pivot pin 122 suitably mounted between the housing halves 24 and 26. The outer ends of the lever 120 are bifuracted, as indicated at 124 and 126, so as to receive therebetween safety pins 128 and 130 respectively forming a part of separate safety cap 132. Cap 132 is normally disposed in a release preventing position at the rear end of the housing halves 24 and 26. In this position pin 128 extends through the centrally apertured end wall 90 into a position within the spring fingers 78 of the collet member 74 thus preventing radially inward deflecting of the spring fingers. Safety pin 130 extends forwardly into a similar position with respect to the second outer tube 118 and the second collet member 114.

The heart monitor assembly 10 and automatic injector assembly 12 are used in carrying out the method of the present invention in the following manner. As previously indicated, the apparatus is provided to targeted coronary prone individuals as part of a treatment method prescribed by the individual's personal physician who also makes arrangements for the individual to be enrolled in the service provided at the central station. As previously indicated the enrollment includes supplying information as to the medical history of the individual and an indication of the personal physician's standing orders when predetermined heart attack symptoms are present in conjunction with predetermined EKG readings.

Each coronary prone individual will be instructed to carry on his person or to have immediately available to his person the monitor assembly 10 and the injector assembly 12. As soon as the individual notices symptoms indicative of a heart attack, as for example a pain in the chest or the like, the individual should immediately make telephone communication with the central station by dialing the number provided. Either immediately before or immediately thereafter, the individual should connect the electrodes 14 and 16 with his person by simply placing them under his armpits, as shown in FIG. 1, and retaining them in such position by his arms. After identifying himself over the telephone to the personnel answering from the central station over the established telephone line, the individual should then bring the housed circuitry 18 into proximity with the transmitting end of the telephone, as shown in FIG. 1, so that the EKG signals produced by the housed circuitry 18 will be transmitted over the telephone line to the central station.

The various procedures which are carried out at the central station include among others the printing of an electrocardiogram based upon the transmitted EKG signals of the individual and a noting of the other heart attack symptoms which the individual may be experiencing through oral communication from the individual over the telephone communication line established. On the basis of this information and the standing orders of the personal physician of the individual, personnel at the central station arrive at a decision as to whether the individual should initiate reperfusion treatment and this decision is transmitted over the telephone line to the individual. Once the individual receives the decision from the central station to initiate the reperfusion treatment the individual then undertakes to operate the injector assembly 12 in the manner shown in FIG. 2.

Prior to the operation of the assembly 12, the individual is instructed with respect to the actuating procedures to be undertaken and the area of the individual's body which is to receive the injection. As shown in FIG. 2, a preferred body area is the calf of one leg. It is within the contemplation of the present invention to utilize other areas, such as a thigh which constitutes the generally accepted area for receiving an injection from an automatic injector calf area is preferred because it provides an unexpected increase in the absorption rate of the dosage 52 contained within the injector assembly 12 in comparison with the absorption rate of the thigh.

It is well known that the thigh area for receiving an intramuscular injection provides a greater resistance to the absorption of the dosage injected into the blood stream than through the deltoid muscle. The deltoid site (in spite of faster absorption) is not satisfactory for human engineering reasons when self-injection is required. Self-injection into the left deltoid by a right-handed person (95% of people are righthanded) is unacceptable for several reasons. The automatic injector which forcefully extrudes the needle about one inch may hit a bone which is highly undesirable. Individuals undergoing the symptoms of a coronary heart attack will often experience pain radiating down the left arm thus providing a practical inhbiition to injecting into that site. Lastly, the deltoid is not a well known area and instructions would have to read "shoulder" which would be non-definitive and further enhance the likelihood of introducing the needle into a bony area like the clavicle or scapula. For these reasons the thigh has been regarded as the site for receiving intramuscular injections when self-injection is indicated, as, for example, the use of automatic injectors to inject chemical warfare antidotes. While the scientific reason of faster absorption within the deltoid as compared with the thigh is not clearly known, applicant has postulated that the reason is because the deltoid is a smaller muscle than the thigh muscle. With this postulate in mid, applicant sought out a more convenient self-injecting site having a smaller muscle than the thigh and tests have shown that injection into the calf muscle provides an absorption rate better than a thigh injection and perhaps as good as the absorption within the deltoid. Moreover, the site is convenient and more readily accessible than the thigh, such accessability being shown by the use of the injector assembly 12 in FIG. 2.

It will be understood that means for enhancing absorption is utilized. For example, it is within the contemplation of the present invention to utilize the electrical stimulation teachings contained in commonly assigned U.S. co-pending application Ser. No. 460,011, filed Jan. 21, 1983.

In accordance with the principles of the present invention, another means for enhancing the absorption rate is to utilize with the t-PA dosage, a dosage of an absorption enhancing agent, such as hydroxylamine hydrochloride. Preferably, the absorption enhancing agent such as hydroxylamine hydrochloride is mixed in with the t-PA dosage to form a single mixed dosage. Although it is within the contemplation of the present invention to inject the absorption enhancing agent as a separate dosage within the same site as the separate dosage of t-PA, preferably through the same needle (e.g. 4,394,863). An example of an amount of absorption enhancing agent, such as hydroxylamine hydrochloride, which is added to the t-PA dosage, as previously described, to form a single mixed dosage is an amount of from 1 to 85 milligrams per kilogram of body weight.

With the preferred calf injection site referred to above, the individual operates the injector assembly 12 to effect the injection by undertaking a predetermined actuating procedure which includes removal of the safety cap 132. The remainder of the actuating procedure includes grasping the exterior of the housing halves 24 and 26 and moving the device 12 with the cap 132 removed so as to engage the forward end of the tubular members 38 and 94 with the portion of the exposed calf muscle as shown in FIG. 2. Continued forward movement of the housing halves 24 and 26 with respect to the calf engaged members 38 and 94 results in the release of the releasing mechanisms 66 and 110. The lever 120 insures that both releasing mechanisms will be actuated irrespective of which of the two are initially released by the aforesaid actuating procedure. That is, if the actuating procedure by the individual is such that the members 38 and 94 are engaged simultaneously, then the respective releasing mechanisms will be simultaneouly released. The operation of the lever 120 is such that if during the aforesaid movement, the members 38 and 94 are sequentially engaged with the calf (in either order) sequential release of the associated releasing mechanisms (in a corresponding order) will occur. To illustrate this sequential operation, it is assumed that in moving the device 12 into engagement with the calf muscle, the member 38 is first engaged and then sequentially the member 94.

The actuation of the releasing mechanism 66 occurs immediately following the engagement of the forward portion 40 of the member 38 with the user's calf. Continued forward movement on the housing halves 24 and 26 results in the forward movement of the cam engaging surface 92 with respect to the cam surfaces 82 of the spring fingers 78. This movement causes the spring fingers to flex inwardly thus moving locking surfaces 80 out of locking engagement with the locking ring 84. Spring 64 is thus released which results in two movements. One is a rearward movement of the inner tube 68 which engages the associated outer tube 88 and moves the latter rearwardly. The rearward movement of the outer tube rear wall 90 has the effect of applying a rearward force to the bifurcated end 124 of the lever 120 thus causing the bifurcated end 126 to move forwardly. This forward movement causes the releasing mechanism 110 to be released in a manner similar to the releasing mechanism 66.

The initial release of spring 64 also creates a main forward force which is applied to the collet member 74 through the lugs 72. This forward force is transmitted by virtue of the spacer 58, plunger 54 and liquid dosage 52 to move the latter together with the container 44, hub 46 and needle 48 forwardly. The forward movement of the needle causes the forward sharpened end thereof to pierce through the resilient sheath 50 and penetrate into the muscle tissue of the calf of the user. The forward movement of the needle 48 and the other components moved forwardly therewith is resisted and stopped by compression of the resilient sheath 50. The continued application of the spring force thereafter creates a sufficiently greater pressure within the liquid dosage 52 to cause the diaphragm within the hub 46 to burst. The liquid dosage 52 is then expelled by the continued forward movement of the spacer 58 and plunger 54 under the applied spring force so as to pass beyond the ruptured diaphragm through the hypodermic needle 48 and outwardly into the muscle tissue of the calf of the user. The cartridge unit 30 functions similarly under the force applied by the released spring 108 when the releasing mechanism 110 is released as aforesaid.

It can thus be seen that the dosages 52 and 98 are easily and conveniently injected into the muscle tissue of the calf of the user in response to a single predetermined actuating procedure which includes removal of the safety cap 132. After injection, the injector assembly 12 is moved rearwardly to withdraw the needles from the muscle tissue of the calf.

While the dual dosage automatic injector assembly 12 described above constitutes a preferred injector assembly in accordance with the principles of the present invention, it will be understood that other multiple dosage automatic injector assemblies may be utilized. For example, in commonly assigned U.S. Pat. No. 4,394,863 there is disclosed a multiple injector assembly providing a single needle and a single container having two dosages therein separated by a plunger. This arrangement utilizing a first dosage containing clot selective coronary thrombolytic agent, such as t-PA mixed with an absorption enhancing agent, such as hydroxylamine hydrochloride, and a second dosage containing cardiac antiarrhythmic agent, such as lidocaine, could be utilized in accordance with the principles of the present invention. Commonly assigned U.S. Pat. No. 4,326,988 illustrates another injector assembly which could be utilized. This patent discloses an assembly consisting of two separate automatic injectors retained in a plural injection assembly. It would be within the purview of the present invention to utilize one automatic injector having a dosage containing clot selective coronary thrombolytic agent, such as t-PA mixed with an absorption enhancing agent, such as hydroxylamine hydrochloride, and another automatic injector having a dosage containing cardiac antiarrhythmic agent, such as liodocaine, in an assembly of this type. Moreover, the present invention contemplates the utilization of two separate automatic injectors containing the two required dosages without convenient assemblage. In its broadest aspects, the invention contemplates other self-injecting assemblies or units which under certain circumstances can be prefilled syringes. Nevertheless, it is greatly preferred to provide the greatest possible simplicity and convenience to the individual undergoing the symptoms of a heart attack because of the existing circumstances and hence an assembly such as described above and shown in the drawings is greatly preferred.

For purposes of completing the background description and present disclosure each of the published articles, patents and patent applications heretofor identified in this specification are hereby incorporated by reference into the specification.

It thus will be seen that the objects of this invention have been fully and effectively accomplished. It will be realized, however, that the foregoing preferred specific embodiment has been shown and described for the purpose of illustrating the functional and structural principles of this invention and is subject to change without departure from such principles. Therefore, this invention includes all modifications encompassed within the spirit and scope of the following claims.

What is claimed is:

1. In a method of initiating life saving treatment of a coronary prone individual undergoing heart attack symptoms at a time during the early minutes or hours after the onset of the heart attack symptoms with the use of a self-injecting unit containing a medicament, said method comprising the steps of determining during the aforesaid time after the onset of heart attack symptoms that the symptoms being experienced by the individual are such as to warrant the injection of said medicament from said self-injecting unit into the individual and then injecting the medicament from said self-injecting unit into the muscle tissue of the individual undergoing the heart attack symptoms, the improvement which renders said method capable of limiting damage to the myocardium of the individual undergoing the heart attack symptoms as a result of coronary thrombosis by establishing reperfusion, said improvement comprising performing the aforesaid steps with a self-injecting unit having a medicament therein which includes a clot selective coronary thrombolytic agent capable of being absorbed into the blood stream from an injection site in the muscle tissue of the individual undergoing the heart attack symptoms in sufficient quantity to establish reperfusion when accomplished within a time sufficiently early after onset of the heart attack symptoms.

2. A method as defined in claim 1 wherein said clot selective coronary thrombolytic agent includes t-PA.

3. A method as defined in claim 2 wherein said medicament also includes an absorption enhancing agent for said t-PA.

4. A method as in claim 3 wherein said absorption enhancing agent is hydroxylamine hydrochloride.

5. A method as defined in claim 3 wherein said medicament also includes a cardiac antiarrhythmic agent.

6. A method as defined in claim 5 wherein said cardiac antiarrythmic agent is lidocaine.

7. A method as defined in claim 1 wherein said medicament also includes a cardiac antiarrhythmic agent.

8. A method as defined in claim 7 wherein said cardiac antiarrythmic agent is lidocaine.

9. A method as defined in claim 1 wherein the injecting step includes injecting the medicament into the muscle tissue of the calf of the individual.

10. In a method of initiating life saving treatment of a coronary prone individual prior to the establishment of qualified direct contact personal care at a time during the early minutes or hours after the onset of heart attack symptoms with the use of apparatus comprising a heart monitoring device and an automatic injector assembly, said heart monitoring device comprising electrode means for connection with the individual in a position to sense the electrical activity triggering the individual's heart beats and means for establishing signals corresponding to the electrical activity sensed by said electrode means capable of being transmitted over a telephone communication line established with a station having information and qualified personnel sufficient to make a decision based upon the signals transmitted and the oral communications transmitted in regard to the individual's symptoms as to the initiation of the treatment by the individual, said automatic injector assembly including releasable force applying means, safety means normally disposed in a release preventing position movable therefrom into a release permitting position, means for separately containing a medicament, hypodermic needle means, and means operable in response to a predetermined manual actuating procedure including the movement of said safety means into said release permitting position for effecting release of said releasable force applying means and causing the released force to be applied so as to effect (1) the movement of said hypodermic needle means into the muscle tissue of the individual undergoing the heart attack symptoms and (2) the flow of medicament within said containing means outwardly thereof through said hypodermic needle means into the muscle tissue of the individual undergoing the heart attack symptoms, said method comprising the steps of: connecting said electroce means to the individual undergoing the heart attack symptoms, establishing a telephone communication line to said station and transmitting thereover the signals established by said signal establishing means, receiving a communication over said telephone communication line indicative of a decision to initiate the treatment, and then performing the predetermined manual actuating procedure with respect to said automatic injector assembly in relation to the individual undergoing the heart attack symptoms so as to (1) move said hypodermic needle means into the muscle tissue of the individual and (2) flow medicament outardly from said containing means through said hypodermic needle means into the muscle tissue of the individual, the improvement which renders said method capable of limiting damage to the myocardium of the individual undergoing the heart attack symptoms as a result of coronary thrombosis by establishing reperfusion, said improvement comprising performing the aforesaid steps with an automatic injector assembly having a medicament therein which includes a clot selective coronary thrombolytic agent capable of being absorbed into the blood stream from an injection site in the muscle tissue of the individual undergoing the heart attack symptoms in sufficient quantity of establish reperfusion when accomplished within a time sufficiently early after onset of the heart attack symptoms.

11. A method as defined in claim 10 wherein said clot selective coronary thrombolytic agent includes t-PA.

12. A method as defined in claim 11 wherein said medicament also includes an absorption enhancing agent for said t-PA.

13. A method as in claim 12 wherein said absorption enhancing agent is hydroxylamine hydrochloride.

14. A method as defined in claim 12 wherein said medicament also includes a cardiac antiarrythmic agent.

15. A method as defined in claim 14 wherein said cardiac antiarrythmic agent is lidocaine.

16. A method as defined in claim 10 wherein said medicament also includes a cardiac antiarrythmic agent.

17. A method as defined in claim 16 wherein said cardiac antiarrythmic agent is lidocaine.

18. A method as defined in claim 10 wherein the injecting step includes injecting the medicament into the muscle tissue of the calf of the individual.

* * * * *